Figure 8:
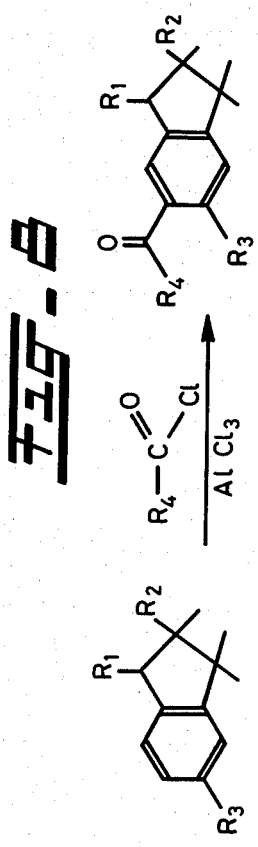
Figure 10:
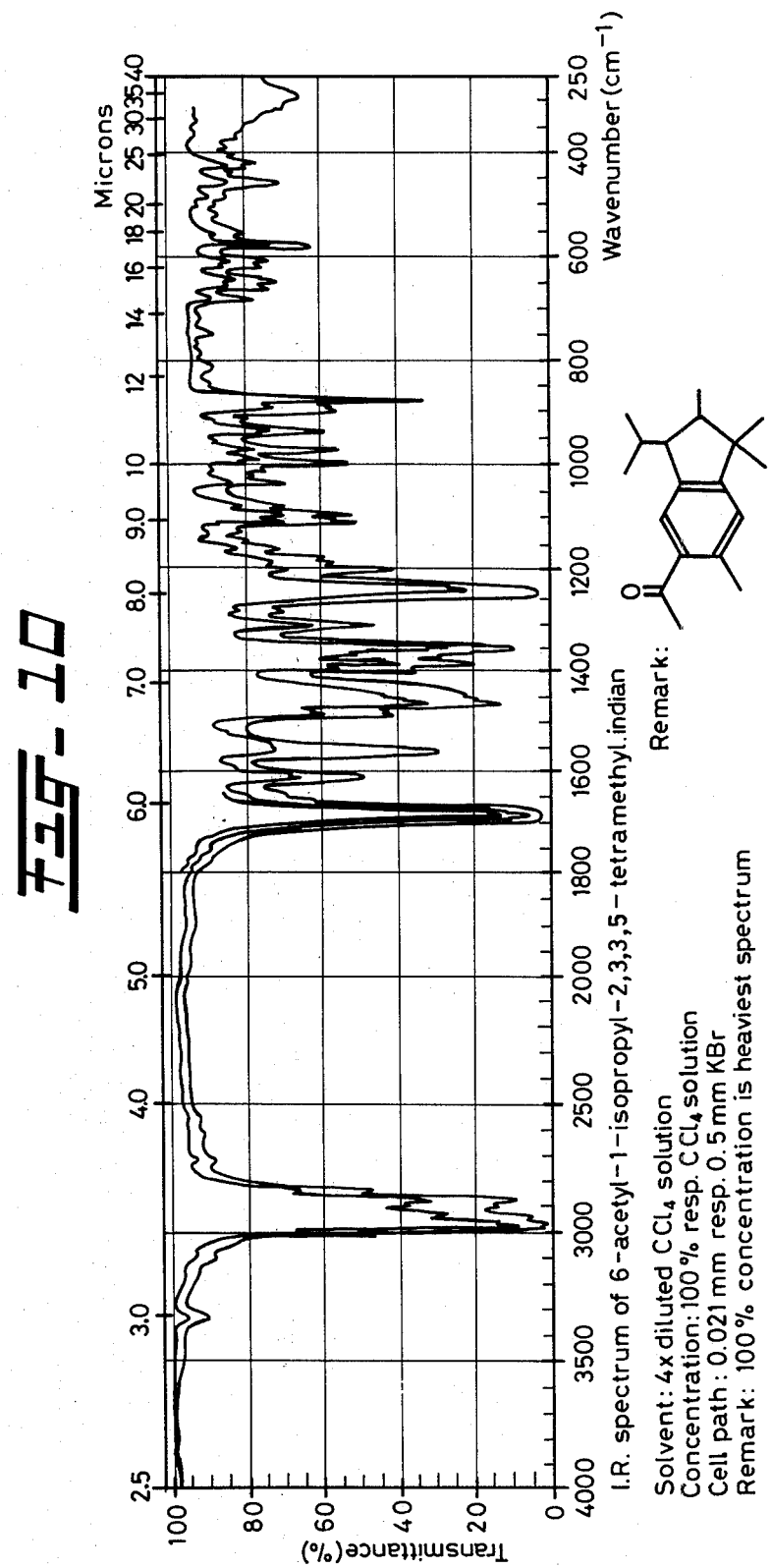

United States Patent [19]

Traas et al.

[11] 4,352,748
[45] Oct. 5, 1982

[54] NOVEL ACYL-POLYALKYLINDAN COMPOUNDS AND THE USE THEREOF AS A BASE FOR PERFUME, AS WELL AS PERFUME COMPOSITIONS

[75] Inventors: Petrus C. Traas, Naarden; Harrie Renes, Bussum; Harmannus Boelens, Huizen, all of Netherlands

[73] Assignee: Naarden International N.V., Netherlands

[21] Appl. No.: 242,841

[22] Filed: Mar. 12, 1981

Related U.S. Application Data

[63] Continuation of Ser. No. 879,509, Feb. 21, 1978, abandoned.

[30] Foreign Application Priority Data

Feb. 25, 1977 [NL] Netherlands .......................... 7702076

[51] Int. Cl.³ .......................... C11D 9/44; C07C 13/30
[52] U.S. Cl. ............................ 252/522 R; 252/174.11; 424/64; 424/65; 424/69; 424/74; 568/327; 568/330
[58] Field of Search ...................... 252/522 R, 174.11; 568/327, 330; 424/64, 65, 69, 74

[56] References Cited

U.S. PATENT DOCUMENTS

| | | | |
|---|---|---|---|
| 2,883,423 | 4/1959 | Mosher et al. | 252/522 R |
| 2,889,367 | 6/1959 | Beets et al. | 252/522 R |
| 3,278,622 | 10/1966 | Stofberg et al. | 585/409 |

FOREIGN PATENT DOCUMENTS

| | | |
|---|---|---|
| 94490 | 1/1960 | Netherlands . |
| 796129 | 6/1958 | United Kingdom . |
| 796130 | 6/1958 | United Kingdom . |

OTHER PUBLICATIONS

T. F. Wood, The Chemistry Of The Aromatic Musks by Givaudan Corp., Clifton N. J., pp. 10-27.
S. H. Weber et al., Rec. Trav. Chim. 74, 1179–1196 (1955); 75, 1433–1444 (1956), 76 193–199 (1957).
D. B. Spoelstra et al. Rec. Trav. Chim. 76, 205–208 (1957); 82, 1100–1106 (1963).
M. Beets et al. Rec. Trav. Chim. 77, 854–871 (1958).

*Primary Examiner*—John F. Niebling
*Attorney, Agent, or Firm*—Brumbaugh, Graves, Donohue & Raymond

[57] ABSTRACT

Novel acyl-polyalkyl indan compounds and the use thereof as a base for perfume, as well as perfume compositions, perfumed materials and perfumed articles.

2 Claims, 20 Drawing Figures

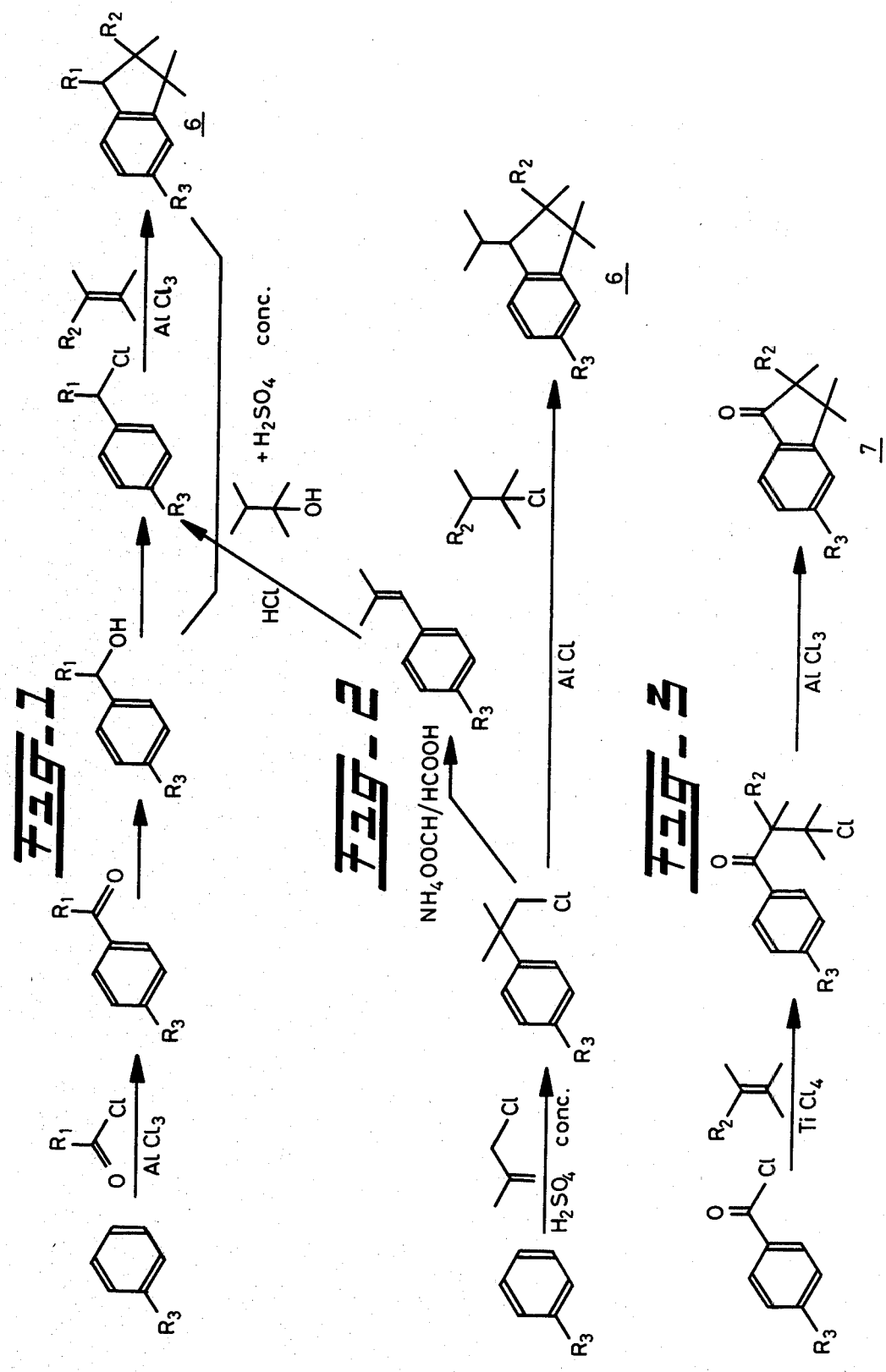

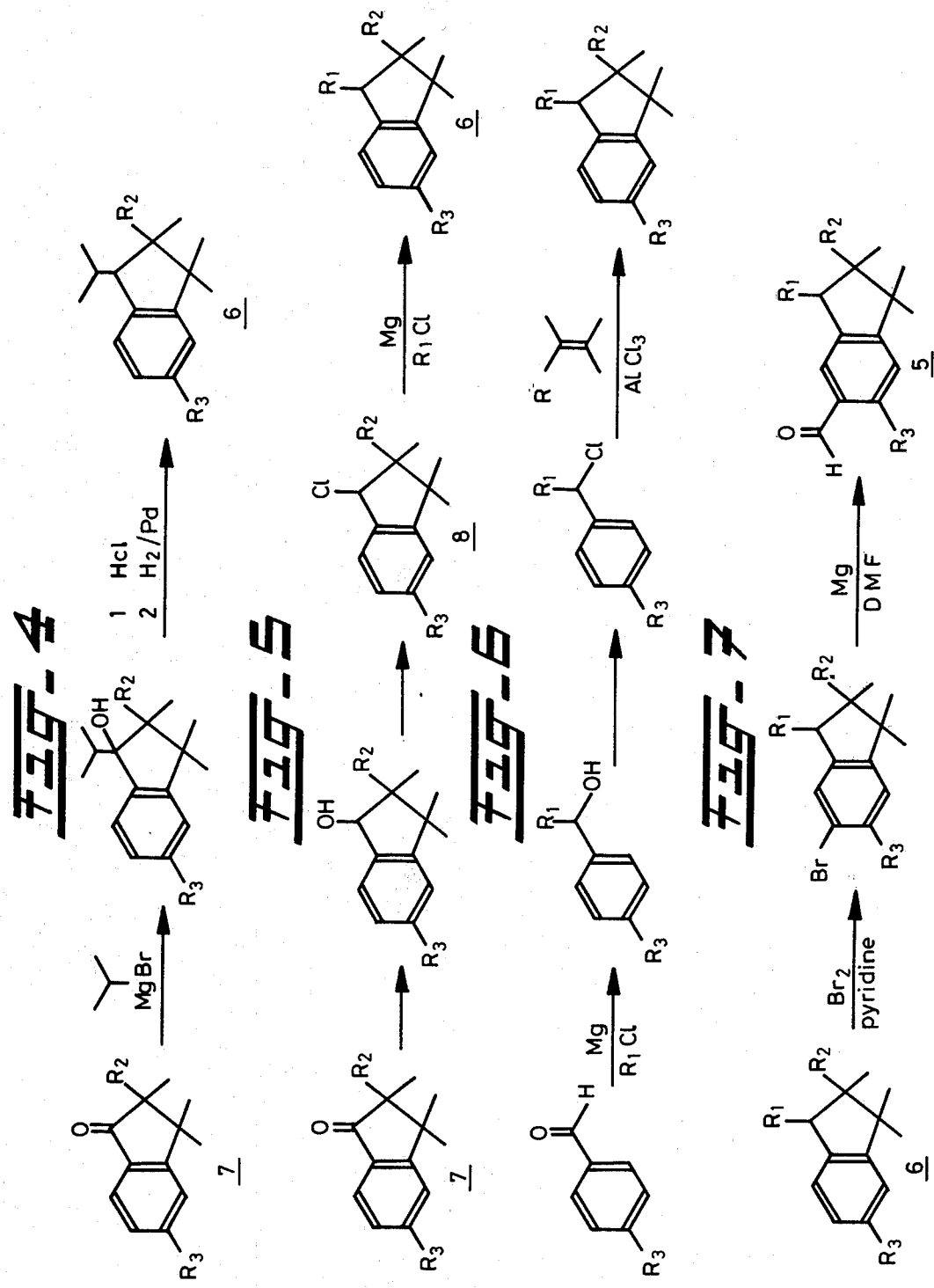

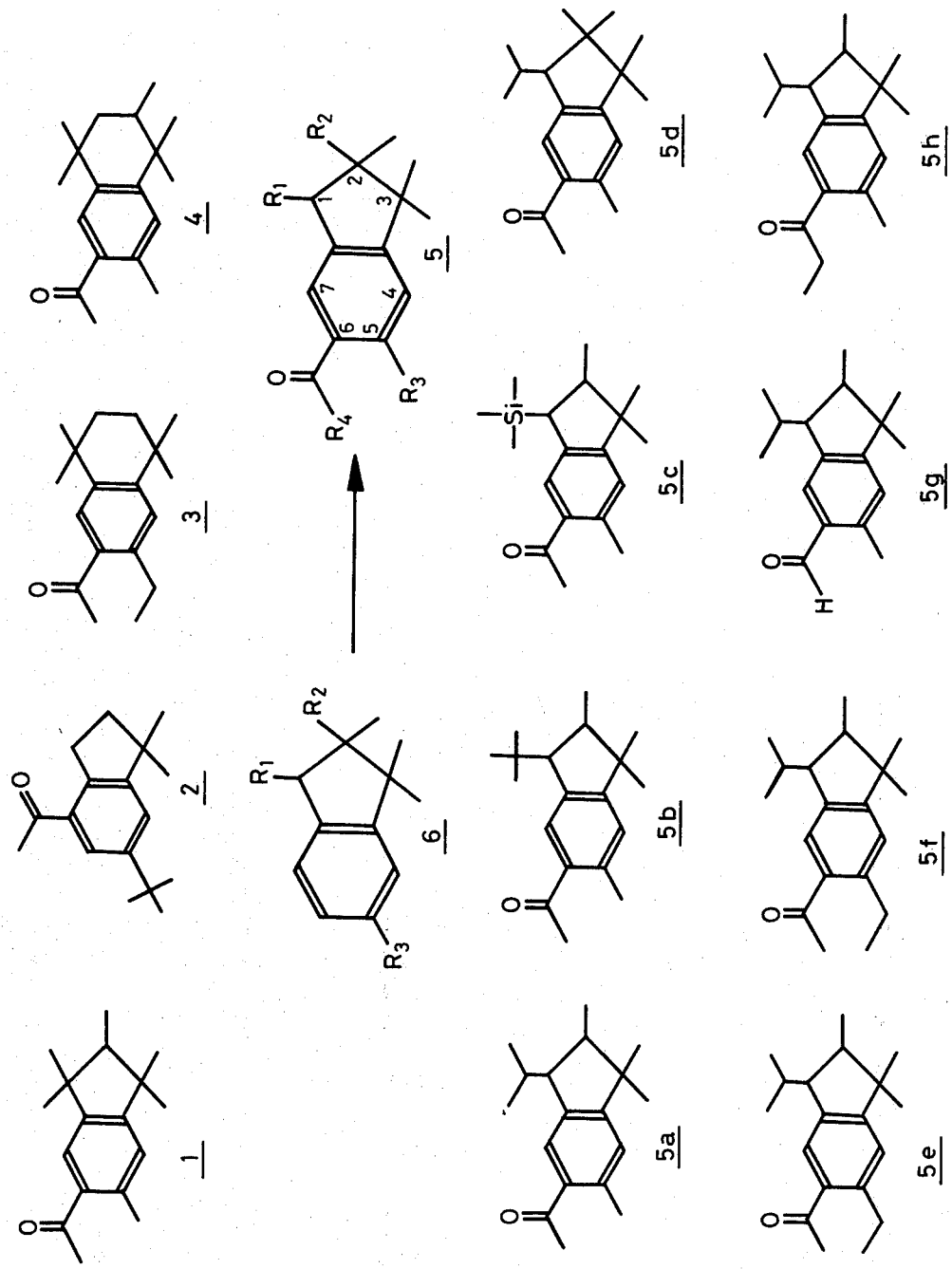

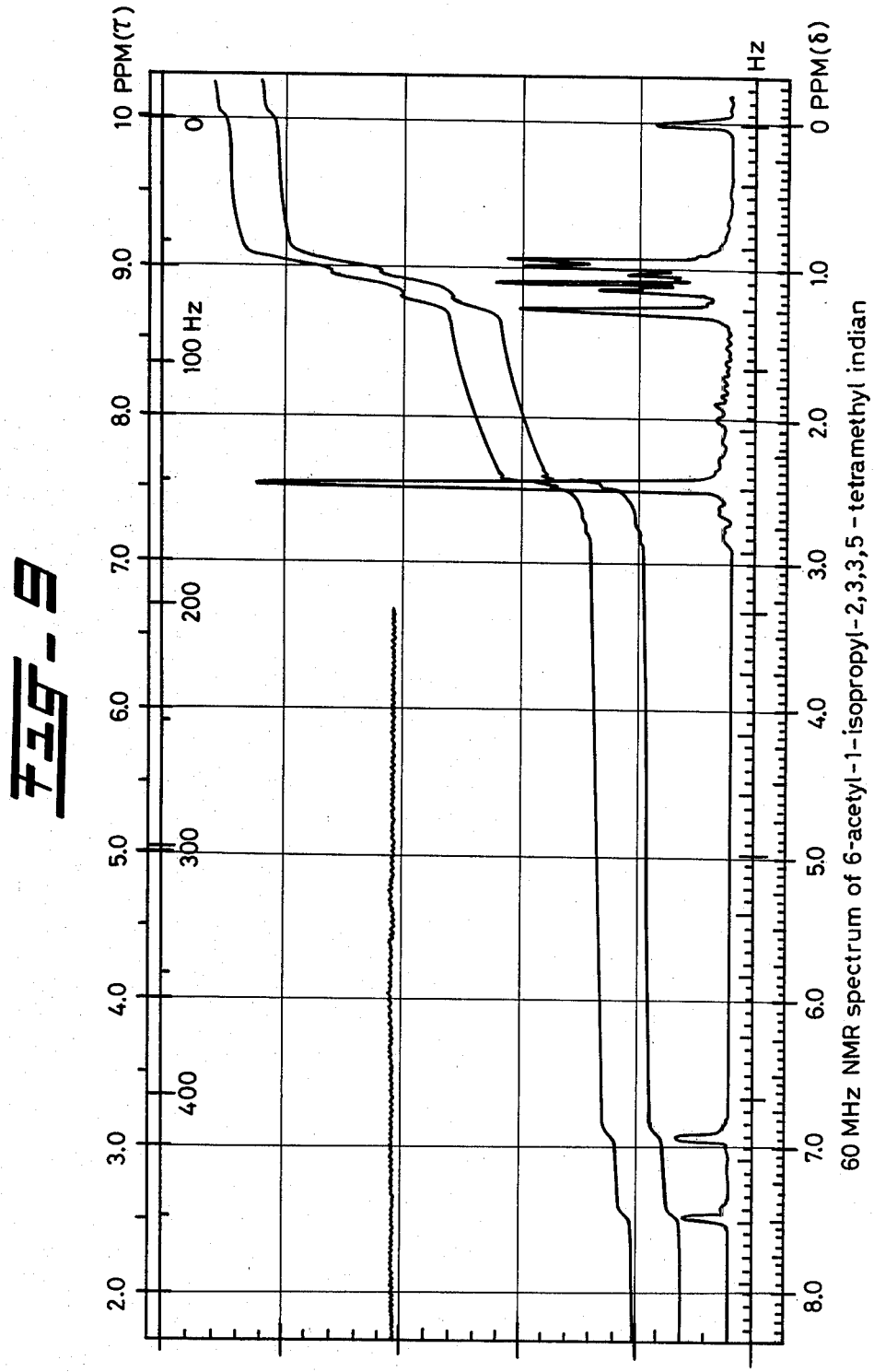

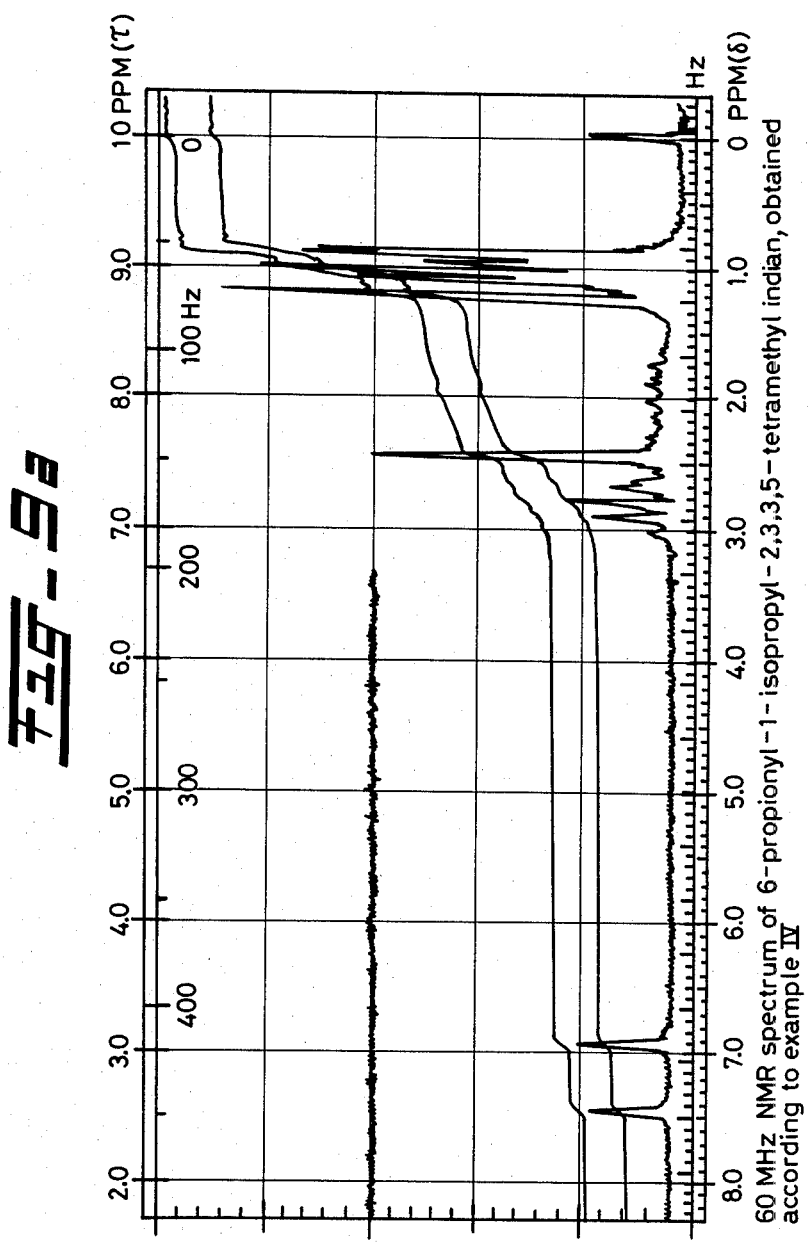

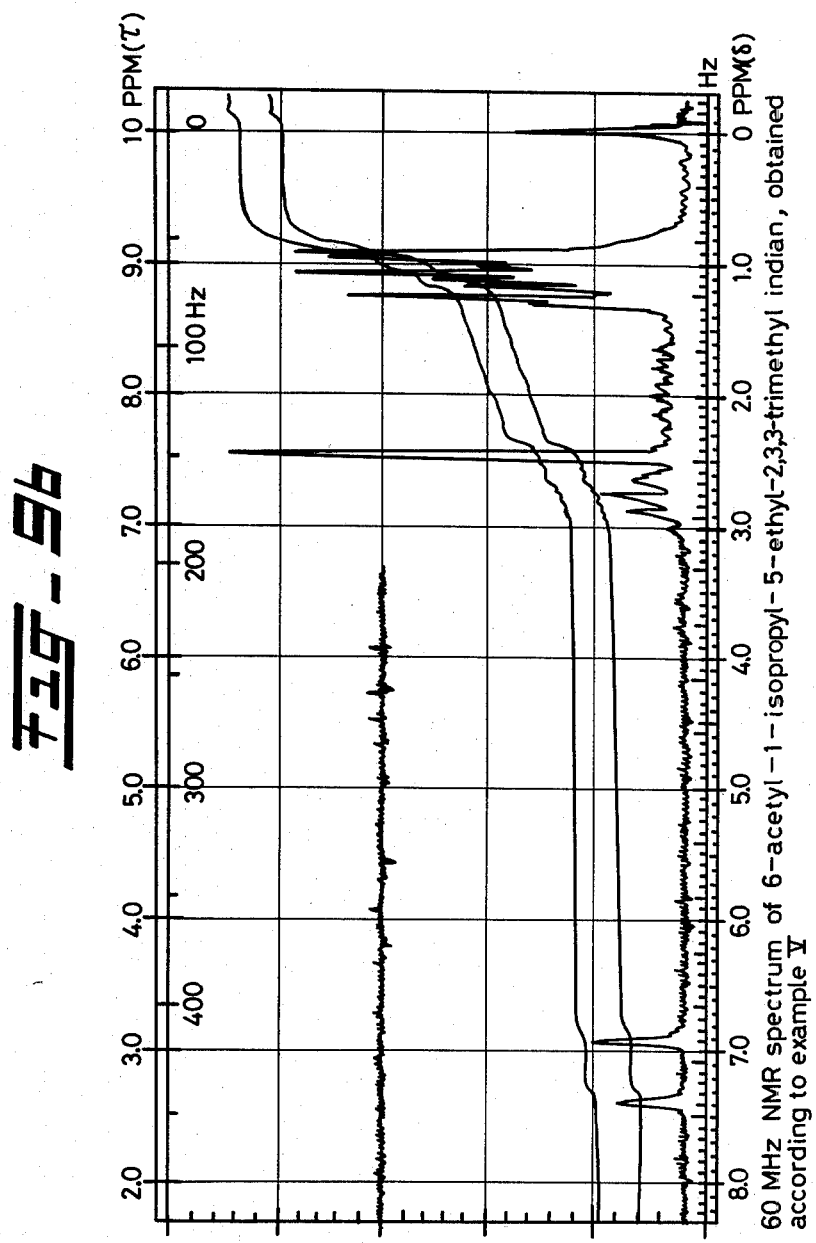

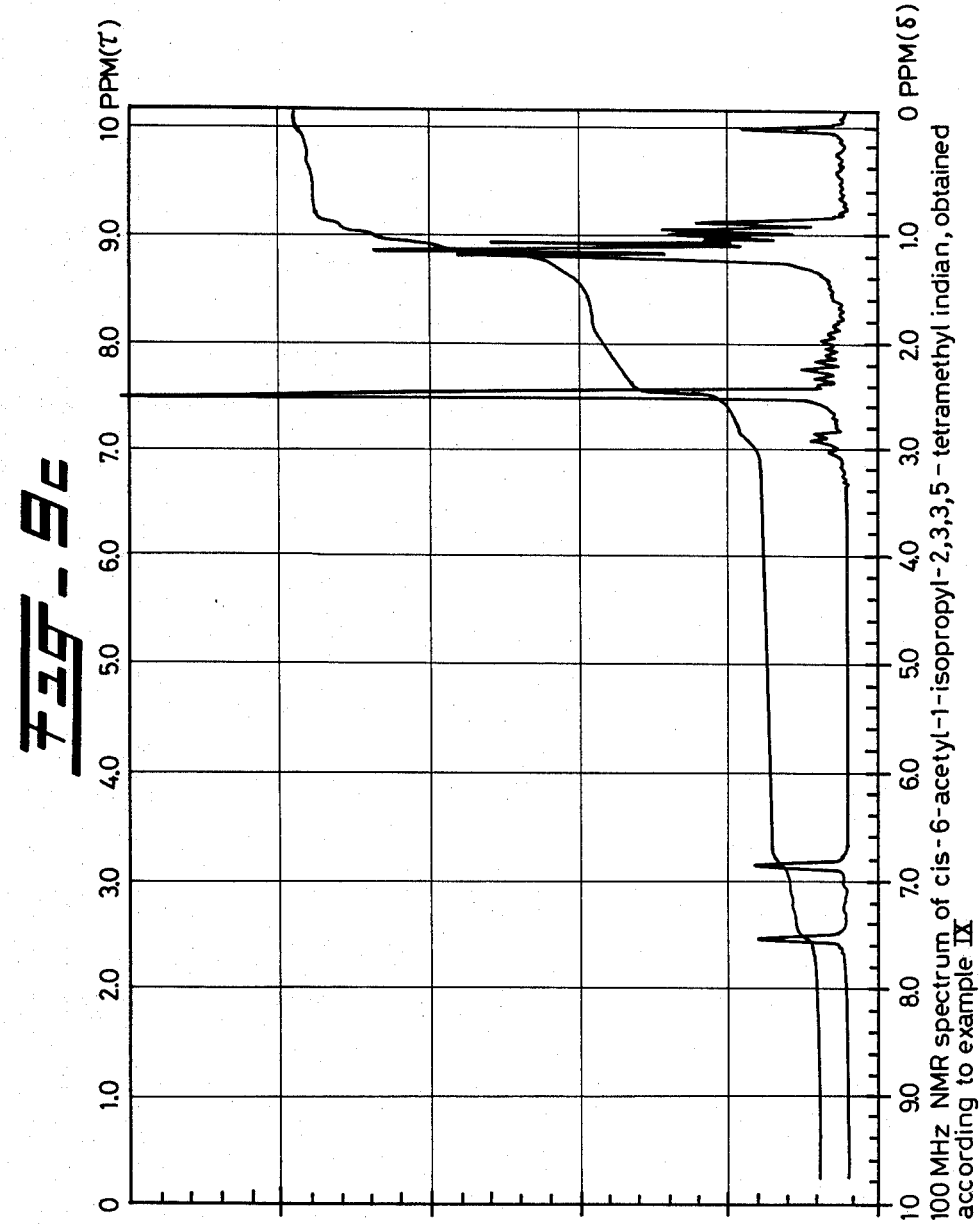

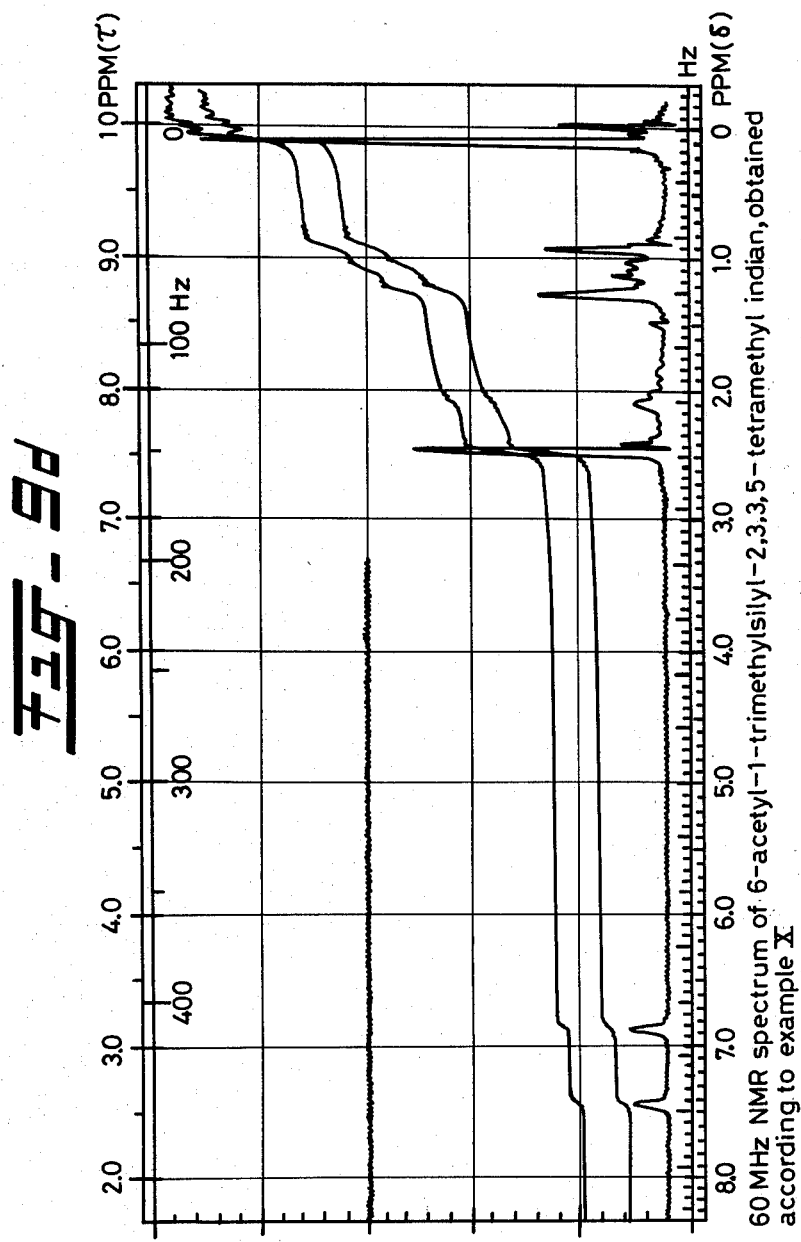

I.R. spectrum of 6-acetyl-1-isopropyl-2,3,3,5-tetramethyl.indian

Solvent: 4×diluted CCl₄ solution
Concentration: 100% resp. CCl₄ solution
Cell path: 0.021 mm resp. 0.5 mm KBr
Remark: 100% concentration is heaviest spectrum

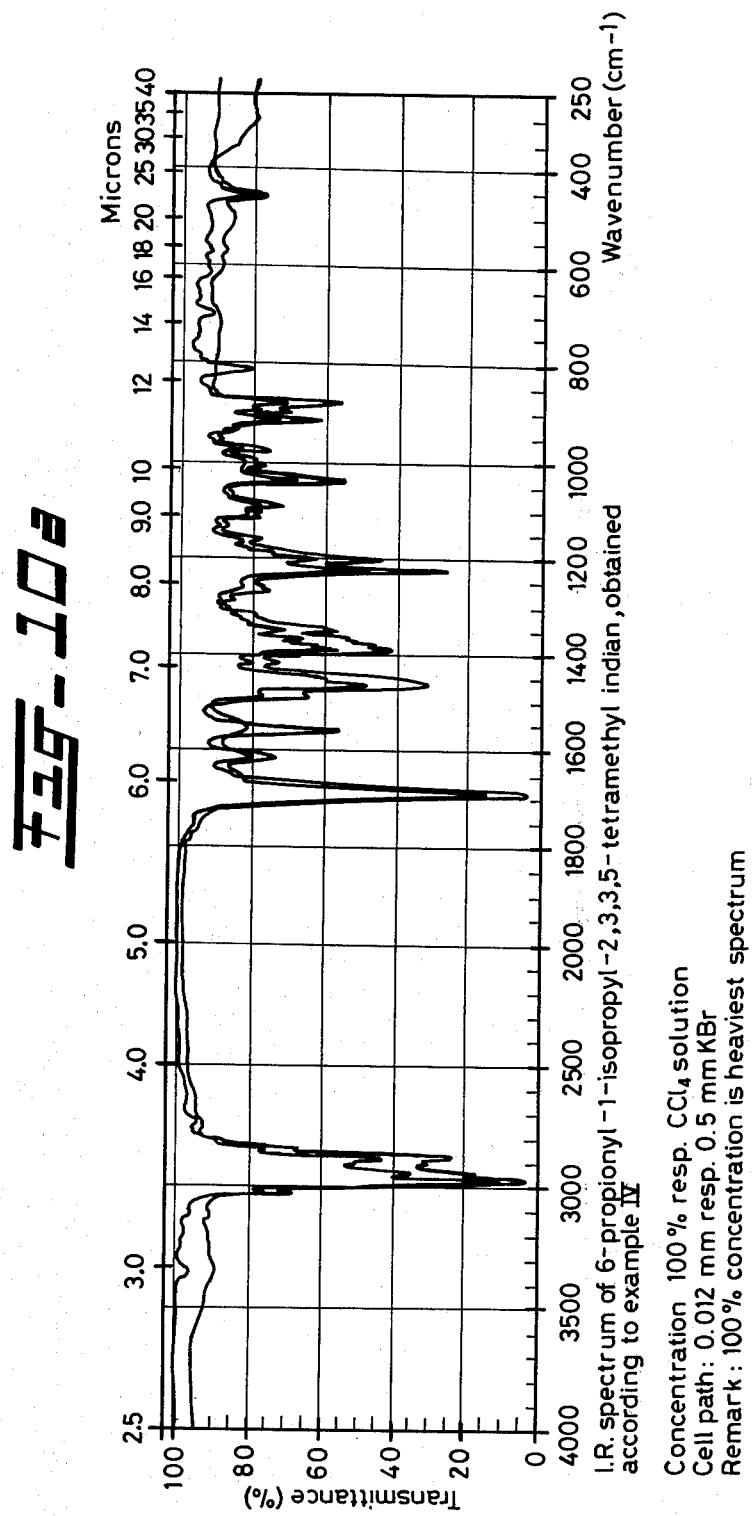

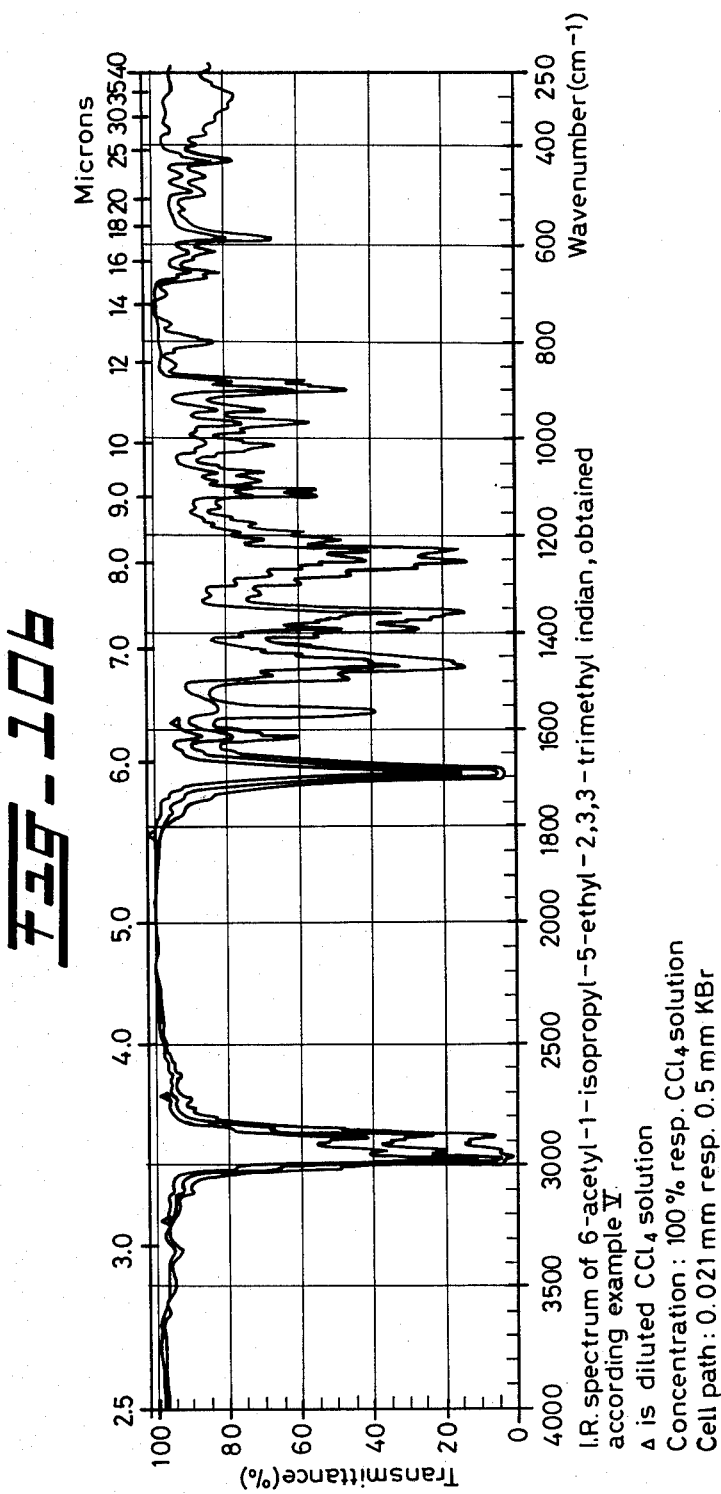

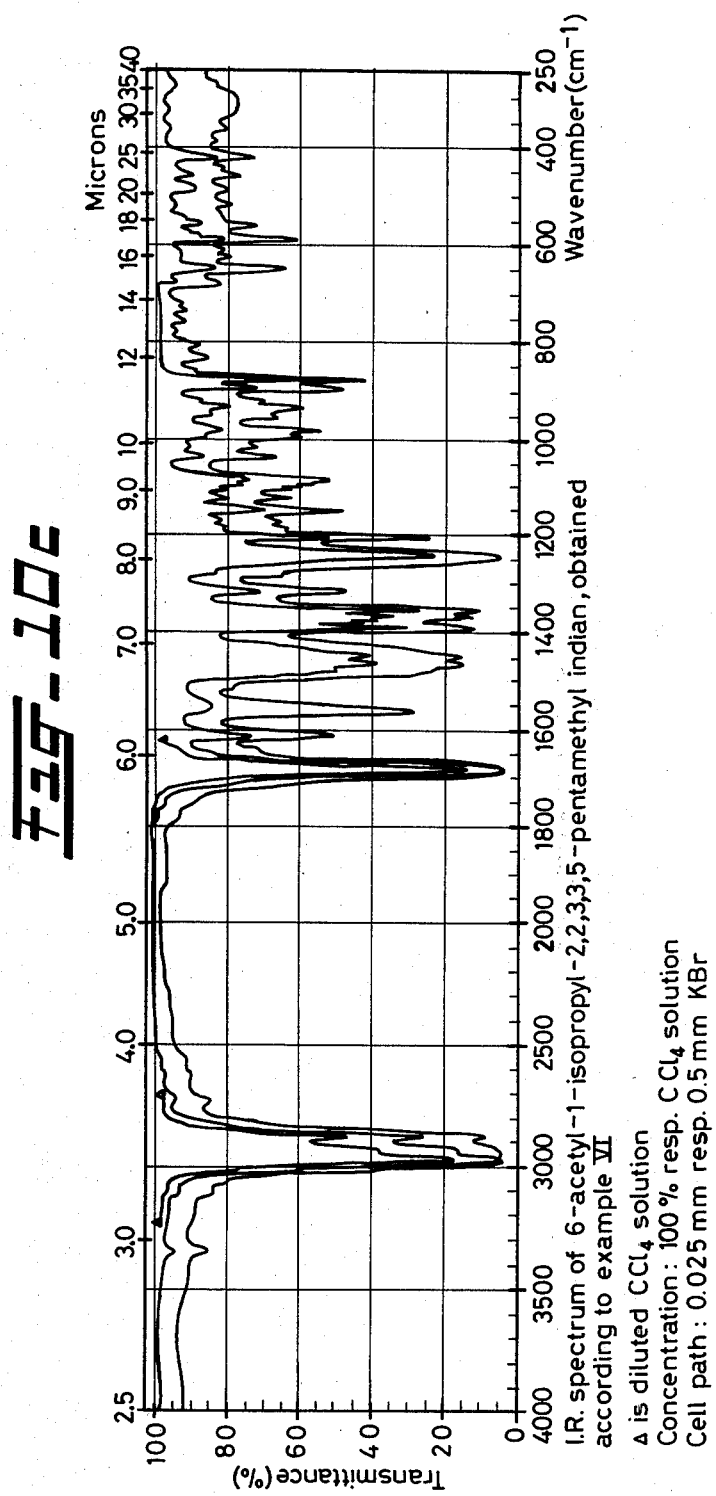

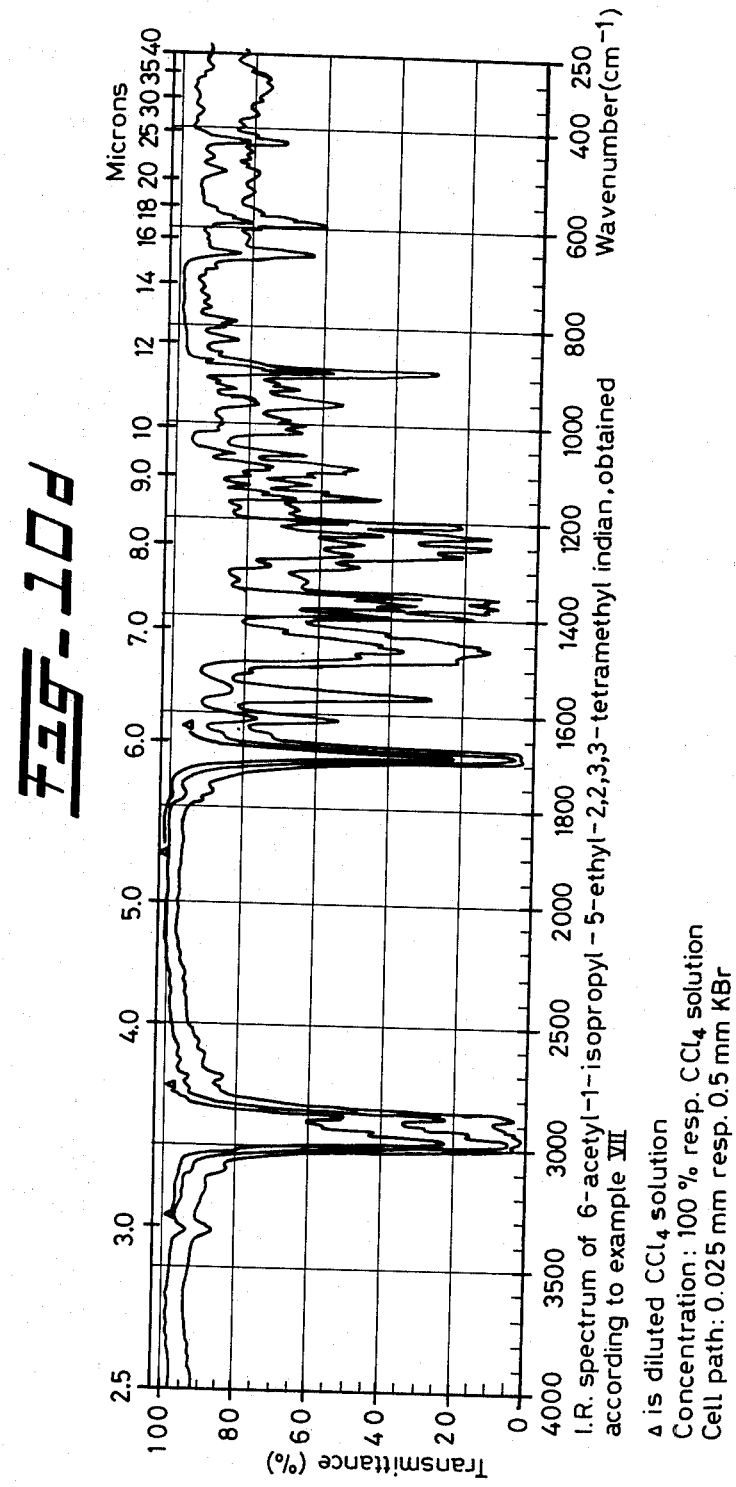

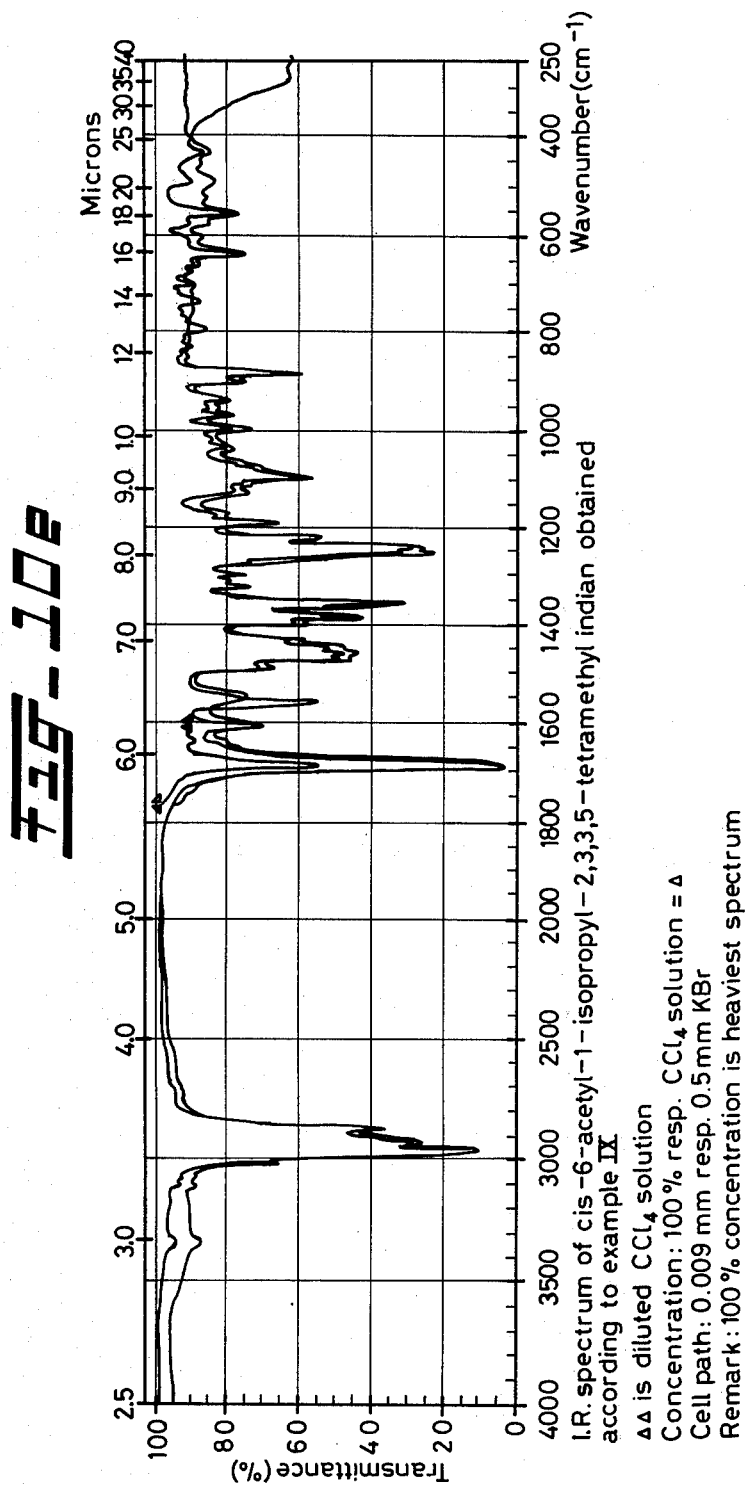

NOVEL ACYL-POLYALKYLINDAN COMPOUNDS AND THE USE THEREOF AS A BASE FOR PERFUME, AS WELL AS PERFUME COMPOSITIONS

This application is a continuation of U.S. application Ser. No. 879,509 filed Feb. 21, 1978 now abandoned.

The invention relates to novel acyl polyalkyl indan compounds, the use thereof as a base for perfume, perfume compositions containing these novel compounds, articles perfumed with these compounds as well as a process for preparing the novel compounds.

There is a continual demand for fragrances having a musk odour. Though the macrocyclic musk fragrances of natural and synthetical origin are generally considered as the best and most natural smelling musk odours, they are too expensive and/or insufficiently stable for most applications.

Therefore there was and there still is a great demand for good musk fragrances which can be synthetized from easily accessible raw materials and which additionally are stable in agressive media such as soaps and detergents like washing agents. To meet this demand there have been developed aromatic musk fragrances, particularly nitroaromatic fragrances, polyalkyl indan, polyalkyl tetralin and isochroman fragrances.

In the years between 1950 and 1965 many acyl-polyalkyl indan and acyl-polyalkyl tetralin compounds have been prepared and examined with regard to their fragrance properties.

Many acyl-polyalkyl indan compounds have been described, e.g. in:

1 Rec. Trav. Chim. 74, 1179–1196 (1955).
2 Rec. Trav. Chim. 75, 1433–1444 (1956).
3 Rec. Trav. Chim. 76, 193–199 (1957).
4 Rec. Trav. Chim. 76, 205–208 (1957).
5 Rec. Trav. Chim. 82, 1100–1106 (1963).
6 British Pat. No. 796,129.
7 British Pat. No. 796,130.
8 Rec. Trav. Chim. 77, 854–871 (1958).
9 T. F. Wood, The Chemistry of the Aromatic Musks, edited by Givaudan Corporation, Clifton, N.J., particularly pages 10–27.
10 Dutch Pat. No. 94,490.

In these publications dozens of acyl-polyalkyl indans as well as in the publications 8 and 9 also acyl-polyalkyl tetralins have been described, all of which have been examined with respect to their fragrance properties.

It appears that from this multitude of data some general rules can be derived, to which acyl-polyalkyl indans have to meet to possess a reasonable strong musk odour. It turns out to be desirable that the alkyl substituents in the non-aromatic ring of the idan frame are methyl groups.

The introduction of an ethyl group involves a clear drop in the odour strength and even bigger alkyl groups result in odourlessness of the compounds: see e.g. the literature references 1, page 1187; 2 page 1439; 9 page 12, FIG. 5 and page 13, FIG. 7.

Further it appears to be necessary that the aromatic ring is substituted with two quaternary carbon atoms. Both of these may form part of the non-aromatic ring, but one of the two can also be introduced in the aromatic ring as a separate tert.alkyl group, see e.g. literature references 8, page 861; 9, page 12, FIGS. 5 and 6; 10, column 2 line 35—column 3 line 10.

However, many of the described compounds, which do meet these conditions, still are unsuitable as a musk fragrance, because they are too weak yet, or because they possess other, undesired odour notes besides a musk odour.

Practice has shown, that of the many dozens of compounds, which have been tested, only two acyl-polyalkylindans and two acyl-polyalkyltetralins are of real interest as a musk fragrance. These compounds, which are indicated with 1, 2, 3 and 4 on the formula sheet, are put on the market by various manufacturers. They all meet the rules mentioned before. Since the middle of the sixties no new developments have been reported in the field of the acyl-polyalkylidans and acyl-polyalkyltetralins, except some new synthesis methods for the four mentioned musk fragrances already known. Experts regard the field as fully explorated.

However, it was surprisingly found that the group of novel compounds, characterized by the general formula 5 of the formula sheet, wherein $R_1$ represents isopropyl, tert.butyl or trimethylsilyl, $R_2$ represents hydrogen or methyl, $R_3$ represents methyl or ethyl and $R_4$ represents hydrogen or methyl or ethyl, are valuable fragrance compounds with a powerful and long-holding musk odour closely approximating that of the macrocyclic musk fragrances. These compounds are distinguished from the known acyl-polyalkylindan musk fragrances because in contravention of the above rules they (a) do not possess two quaternary carbon atoms, but only one quaternary and one tertiary carbon atom directly adjacent to the benzene ring;

(b) are not substituted exclusively with mehyl groups, but are characterized in possessing a much larger substituent on the cyclopentane ring.

Examples of compounds covered by the general formula 5 and so making part of the invention are:

6-acetyl-1-isopropyl-2,3,3,5-tetramethyl indan (5a)
6-acetyl-1-tert.butyl-2,3,3,5-tetramethyl indan (5b)
6-acetyl-1-trimethylsilyl-2,3,3,5-tetramethyl indan (5c)
6-acetyl-1-isopropyl-2,2,3,3,5-pentamethyl indan (5d)
6-acetyl-1-isopropyl-5-ethyl-2,2,3,3-tetramethyl indan (5e)
6-acetyl-1-isopropyl-5-ethyl-2,3,3-trimethyl indan (5f)
6-formyl-1-isopropyl-2,3,3,5-tetramethyl indan (5g)
6-propionyl-1-isopropyl-2,3,3,5-tetramethyl indan (5h)

The unique character of the group of compounds according to the invention also appears from the fact that many related compounds, which, however, do not comply with the general formula 5, possess no or only a very weak musk odour and therewith do meet the general rules which were deducible from the prior art. For example, 6-acetyl-1-isopropyl-3,3,5-trimethyl indan has a somewhat fruity, but not a bit of a musk, odour, 6-acetyl-1-isopropyl-5-ethyl-3,3-dimethyl indan has a desinfection odour, 6-acetyl-1-isopropyl-2-ethyl-3,3,5-trimethyl indan has a very weak musk odour, 6-acetyl-1-isopropyl-2,5-diethyl-3,3-dimethyl indan has an unpleasant odour reminiscent of hydrogen sulphide and 6-isobutyroyl-1-isopropyl-2,3,3,5-tetramethyl indan also has an unpleasant odour.

The compounds according to the invention can be synthetized according to various ways known per se for such compounds, preferably by acylating the corresponding polyalkylindans (formula 6 of the formula sheet). In turn these polyalkyl indans can be prepared by known methods. Examples of such methods are given in the reaction schemes according to FIGS. 1–6.

According to reaction scheme FIG. 1 toluene or ethylbenzene is subjected in a usual way to a Friedel-Crafts acylation to form p-tolyl-isopropyl ketone and p-ethylphenyl isopropyl ketone ($R_1$=isopropyl) respectively. Then the ketone is reduced in a known way to form the corresponding alcohol, e.g. with a complex metal hydride such as $NaBH_4$ or by way of a Meerwein-Ponndorf type reaction with aluminium isopropylate. The alcohol is reacted in a known way, e.g. with gaseous HCl or with $SOCl_2$ in pyridine, to form the corresponding chloride. After that this compound is condensated with trimethyl ethene or 2-methyl-2-butylchloride, respectively with tetramethyl ethene or with 2,3-dimethyl-2-butyl chloride, under the influence of a Lewis acid such as $AlCl_3$ or $TiCl_4$, to form the desired polyalkyl indan having the formula 6 (wherein $R_1$=isopropyl). If required the aforesaid alcohol can directly be converted into the desired polyalkyl indan by reaction with trimethyl or tetramethyl ethene under the influence of $AlCl_3$ or concentrated sulphuric acid or by reaction with 2-methyl-2-butanol, respectively 2,3-dimethyl-2-butanol under the influence of concentrated sulphuric acid. If the first Friedel-Crafts acylation is conducted with pivaloyl chloride instead of isobutyroyl chloride the corresponding tert.butyl polyalkyl indan (formula 6 with $R_1$=tert.butyl) is obtained.

The compounds wherein $R_1$=isopropyl can also be prepared from p-methyl or p-ethyl neophyl chloride according to FIG. 2. The neophyl chloride can be obtained in a known way by condensating toluene (resp. ethyl benzene) with methallyl chloride in a strong acid medium like concentrated sulphuric acid. If neophyl chloride is condensated with trimethyl ethene or with 2-methyl-2-butyl halide, respectively with tetramethyl ethene or 2,3-dimethyl-2-butyl halide under the influence of a Lewis acid such as $TiCl_4$ or $AlCl_4$ first a rearrangement takes place, through which after condensation and ring closure directly the desired 1-isopropyl-polyalkyl indan (formula 6, $R_1$=isopropyl) is formed.

By treating the para-substituted neophyl chloride with a mixture of ammonium formiate and formic acid it rearranges to form para-substituted 1-phenyl-2-methyl propene, that is converted into para-substituted 1-phenyl-2-methyl-1-propyl chloride by addition of HCl. In turn this can further react to the desired indan according to the scheme of FIG. 1.

The compounds according to the invention can also be prepared from the indanone having the formula 7, which in turn can be synthetized in a known way according to the scheme of FIG. 3.

The indanone with the formula 7 can be converted into the polyalkyl indan having the formula 6, wherein $R_1$=isopropyl, e.g. by reaction with isopropyl magnesium bromide followed by reaction with HCl, dehydrohalogenation and catalytic hydrogenation (FIG. 4). On the other hand the indanone having the formula 7 can also be converted into the indanyl chloride having the formula 8 after reduction to the corresponding alcohol (FIG. 5). This compound can be converted into the desired polyalkyl indans having the formula 6 by reaction with magnesium and isopropyl chloride, tert.butyl chloride or trimethylsilyl chloride, respectively. Finally the polyalkyl indans having the formula 6, wherein $R_1$=isopropyl or tert.butyl can be prepared from p-methyl or p-ethyl benzaldehyde, starting with a Grignard reaction, according to the scheme of FIG. 6. Further this way of preparation is analogous to FIG. 1.

The polyalkyl indans having the formula 6 prepared according to FIGS. 1-6 can be acylated to the acyl-polyalkyl indan having the formula 5 according to the invention in ways known per se.

According to the scheme of FIG. 7 thus a formyl group can be introduced by brominating, followed by a Grignard reaction, e.g. with dimethyl formamide. The acetyl and propionyl group can be introduced by a Friedel-Crafts acylation e.g. with the desired acylhalide under the influence of a Lewis acid, such as $AlCl_3$. According to the reaction scheme of FIG. 8 it is possible to carry out condensation and ring closure according to FIG. 1 and acylating according to FIG. 7 or 8, successively in the same solvent, e.g. nitromethane, nitromethane/cyclohexane or nitrobenzene, without isolating the polyalkyl indan having the formula 6.

With the mentioned methods of preparation the compounds according to the invention are obtained as mixtures of the various cis, trans and stereo isomers. These isomers can be separated according to methods known per se, e.g. gas-liquid-chromatography.

The cis-trans-ratio (concerning the groups $R_1$ and the adjacent methyl group if $R_2$=H) in the reaction mixture depends on the nature of the group $R_1$ and the followed way of preparation.

It appears to be that the product of the synthesis according to FIG. 1 for $R_1$=isopropyl en $R_2$=H contains 90-95% trans and 5-10% cis compound. On the other hand the synthesis according to FIG. 4 for $R_2$=H gives approximately 85% cis and 15% trans product. Usually the olfactic properties of the cis and trans isomers are not fully identical, e.g. the odour of trans-5a is evidently more powerful than that of cis-5a. However, in practice a separation of the isomers does not appear to be necessary and the mixture of isomers obtained by the preparation can be directly used as a fragrance.

As mentioned before the compounds according to the invention are powerful and stable fragrances with a pronounced musk odour. Yet there are evident differences in odour strength and odour character among the compounds mutually. For example, the compounds of the formula 5a and 5c both have a very strong musk odour, where 5a possesses also a slightly fruity note. For compound 5f the musk character is somewhat weaker and the fruity note somewhat stronger than for 5a. Compound 5g has a slightly earthy, geosmin like note besides the dominating musk odour. Compounds with $R_1$=isopropyl are preferred.

The compounds according to the invention can be used as such as an odour imparting substance or may be used successfully in perfume compositions.

By the phrase "perfume composition" a mixture of fragrance and possibly auxiliary substances is meant, said mixture being dissolved, if desired, in an appropriate solvent or mixed with a powdered substrate which is used to impart a desired odour to the skin and/or to all kinds of products.

Such products are e.g.: soaps, detergents, washing agents and cleaners, air refreshers and room sprays, pommanders, candles, cosmetics such as creams, ointments, toilet waters, pre- and aftershave lotions, talcum powders, products for hair care, body deodorants and anti-perspirants.

Fragrances and mixtures of fragrances which can be used in preparing perfume compositions may include natural products like essential oils, absolues, resinoids, resins, concretes etc., but may also include synthetical fragrances like hydrocarbons, alcohols, aldehydes, ketones, ethers, acids, esters, acetals, ketals, nitrils etc., including saturated and unsaturated compounds, aliphatic, carbocyclic and heterocyclic compounds. Examples of fragrance compounds, which may be used in combination with the compounds according to the invention are: geraniol, geranyl acetate, linalool, linalyl acetate, tetrahydrolinalool, citronellol, citronellyl acetate, myrcenol, myrcenyl acetate, dihydromyrcenol, dihydromyrcenyl acetate, tetrahydromyrcenol, terpineol, terpinyl acetate, nopol, nopyl acetate, β-phenylethanol, β-phenylethyl acetate, benzyl alcohol, benzyl acetate, benzyl salicylate, benzyl benzoate, amyl salicylate, styrallyl acetate, dimethylbenzylcarbinol, trichloromethylphenylcarbinyl acetate, p-tert.butyl-cyclohexyl acetate, isononyl acetate, vetiverylacetate, vetiverol, α-hexyl-cinnamic aldehyde, α-n.pentyl-cinnamic aldehyde, 2-methyl-3-(p-tert.butylphenyl)-propanal, 2-methyl-3-(p-isopropylphenyl)-propanal, 3-(p-tert.butylphenyl)propanal, tricyclododecenyl acetate, tricyclododecenyl propionate, 4-(4-hydroxy-4-methyl-pentyl)-cyclohex-3-ene carbaldehyde, 4-(4-methyl-3-pentenyl)-cyclohex-3-ene carbaldehyde, 4-acetoxy-3-pentyl-tetrahydropyran, 3-carboxymethyl-2-pentyl-cyclopentane, 2-n.heptylcyclopentanone, 3-methyl-2-pentyl-3-cyclopentanone, 2-hexyl-2-cyclopentenone, n-decanal, n-dodecanal, 9-decenol-1, phenoxyethyl isobutyrate, phenylacetaldehyde dimethyl acetal, phenylacetaldehyde diethyl acetal, geranyl nitril, citronellyl nitril, cedryl acetate 3-isocamphyl-cyclohexanol, cedryl methyl ether, isolongifolanone, aubepine nitril, aubepine, heliotropine, coumarin, eugenol, vanilline, diphenyl oxide, hydroxycitronellol, ionones, methyliononen, isomethyliononen, irones, cis-3-hexenol and its esters, indan musks, tetralin musks, isochromane musks, macrocyclic ketones, macrolactone musks, ethylene brassylate, aromatic nitromusks.

Auxiliary substances and solvents which may be used for the preparation of perfume compositions which contain compounds according to the invention include solvents like ethanol, isopropanol, diethylene glycol monoethyl ether, diethyl phthalate etc.

The amount of indan fragrance according to the invention to be used in a perfume composition or in a product to be perfumed may vary within large limits and is i.a. dependent on the product wherein the fragrance is used and on the nature and the amount of the other components of the perfume composition and the odour effect to be achieved. Therefor it is only possible to give very rough limits, from which the expert, however, can get an impression concerning the odour strength and the possibilities of application of the indan fragrances according to the invention. In most cases an amount of only 0.01% by weight may be sufficient to impart a slight, but distinctly perceptible musk note to a perfume composition or a product to be perfumed. Of course, this concentration is proportionally lower in so-called extrait-perfumes and in products perfumed with the aid of perfume compositions, the concentration being dependent on the amount of perfume composition used in the end-product. In all applications the upper limit of the amount of fragrance according to the invention is 100% by weight. The so-called musk oils for body perfuming, which are rising in popularity, consist of undiluted musk perfume compositions. The practice air refreshening sticks may contain at most 80% by weight of perfume composition.

The following examples are given to illustrate the possibilities of preparing the described compounds and the applications as fragrances. However, it is to be understood that these examples are not intended to limit the scope of the present invention.

EXAMPLE I

Preparation of i-isopropyl-2,3,3,5-tetramethyl indan, according to the reaction scheme of FIG. 1.

At 10° C. a solution of 75 g $AlCl_3$ in 100 ml nitromethane is added to a mixture of 49 g isobutyroyl chloride, 50 ml nitromethane and 100 ml toluene, after which the mixture is stirred during one hour. Then the reaction mixture is poured out into ice and extracted with ether. The ether solution is washed neutral, dried and evaporated. The residue is distilled under diminished pressure to obtain p-tolyl isopropyl ketone in a yield of 90%. 11 g of this ketone, dissolved in 50 ml methanol, is added to a solution of 10 g $NaBH_4$ in 100 ml methanol/water 1:1. The reaction mixture is stirred during one hour, after that poured out into water and extracted with ether. The solution in ether is dried on $MgSO_4$ and evaporated. Raw 2-methyl-1-(p-tolyl)propanol-1 is obtained in a yield of 97%.

20 ml thionyl chloride is added to 10 g of this alcohol and 2 ml pyridine keeping the temperature at 10°-20° C. Subsequently the reaction mixture is stirred half an hour and then poured out into ice and extracted with ether. The solution in ether is washed neutral, dried and evaporated. The residue is distilled under diminished pressure to obtain 2-methyl-1-(p-tolyl)propyl chloride in a yield of 98%.

At 5°-10° C. a solution of 25 g $AlCl_3$ in 100 ml nitromethane is added to 30 g of this chloride, 15 g trimethyl ethene and 50 ml nitromethane. After that the reaction mixture is stirred during 15 min., poured out into ice and extracted with ether. The solution in ether is washed neutral, dried and evaporated. The residue is distilled under diminished pressure to obtain 1-isopropyl-2,3,3,5-tetramethyl indan in a yield of 80%. B.p. 102°-105° C./1 mm Hg; $n_{20}{}^D = 1,5153$.

The last step of the preparation of this indan can also be effected with $TiCl_4$ and tert.amyl chloride.

EXAMPLE II

Preparation of 1-isopropyl-2,3,3,5-tetramethyl indan according to the reaction scheme of FIG. 2

24 g Methallyl chloride is added to a mixture of 92 g toluene and 49 g concentrated sulphuric acid, keeping the temperature at 40° C. No exothermal reaction occurs. Subsequently the reaction mixture is stirred during half an hour, after which the layers are separated. The organic layer is washed neutral with soda solution, dried on $MgSO_4$ and evaporated. The residue is distilled under diminished pressure to obtain 2-methyl-2-(p-tolyl)-propyl chloride (p-methyl-neophyl chloride) in a yield of 85%.

At 5°-10° C. a mixture of 18 g p-methyl-neophyl chloride and 10 g tert.amyl chloride is added to 10 g $AlCl_3$, dissolved in 50 ml nitromethane. Then the reaction mixture is allowed to warm up to room temperature and stirred during one hour. The reaction mixture is poured out into ice and then extracted three times with ether.

The solution in ether is washed neutral, dried on $MgSO_3$ and evaporated. The residue is distilled under diminished pressure to obtain 1-isopropyl-2,3,3,5-tetramethyl indan in a yield of 31%. B.p. 102°-105° C./1 mm Hg; $n_{20}{}^D = 1,5153$.

The same product is obtained when the condensation is effected identically with TiCl₄ and tert.amyl chloride or with AlCl₃ or TiCl₄ and trimethyl ethene.

EXAMPLE III

Preparation of 6-acetyl-1-isopropyl-2,3,3,5-tetramethyl indan according to the reaction scheme of FIG. 8

At 0°–5° C. a solution of 4 g AlCl₃ in 50 ml nitromethane is added to a mixture of 6 g 1-isopropyl-2,3,3,5-tetramethyl indan (obtained according to example I or II) and 25 g acetyl chloride. Then the reaction mixture is stirred at room temperature during 30 min. and poured out into ice and extracted three times with ether. The solution in ether is washed neutral, dried and evaporated. The residue is distilled under diminished pressure to obtain 6-acetyl-1-isopropyl-2,3,3,5-tetramethyl indan in a yield of 95%. B.p. 144°–146° C./1 mm Hg; $n_{20}{}^D = 1,5301$.

EXAMPLE IV

Preparation of 6-propionyl-1-isopropyl-2,3,3,5-tetramethyl indan according to the reaction scheme of FIG. 8

At 0°–5° C. a solution of 4 g AlCl₃ in 50 ml nitromethane is added to a mixture of 6 g 1-isopropyl-2,3,3,5-tetramethyl indan (obtained according to example I or II) and 25 g propionyl chloride. Then the reaction mixture is stirred at room temperature during one hour and poured out into ice and extracted three times with ether. The solution in ether is washed neutral, dried and evaporated. The residue is distilled under diminished pressure to obtain 6-propionyl-1-isopropyl-2,3,3,5-tetramethyl indan in a yield of 80%. B.p. 145° C./1 mm Hg.

EXAMPLE V

Preparation of 6-acetyl-1-isopropyl-5-ethyl-2,3,3-trimethyl indan according to the reaction schemes of FIG. 1 and FIG. 8

At 10° C. a solution of 93 g (0.72 mol) AlCl₃ in 250 ml nitromethane is added to a mixture of 66 g (0.62 mol) ethyl benzene and 70 g (0.66 mol) isobutyroyl chloride, after which the mixture is stirred during half an hour. The reaction mixture is poured out into ice and extracted with ether. The solution in ether is washed neutral, dried on MgSO₄ and evaporated. The residue is distilled under diminished pressure to obtain p-ethylphenyl isopropyl ketone in a yield of 77%.

84 g of this ketone, dissolved in 200 ml methanol, is added to a solution of 80 g NaBH₄ in 400 ml methanol/water 1:1. Then the reaction mixture is stirred during two hours and after that poured out into water and extracted with ether. The solution in ether is dried on MgSO₄ and evaporated. The residue is added to 200 ml thionyl chloride keeping the temperature at approximately 25° C. The reaction mixture is then stirred during half an hour, poured out into ice and extracted with ether. The solution in ether is washed neutral with soda solution, dried on MgSO₄ and evaporated. The residue is distilled to obtain 80 g 2-methyl-1-(p-ethylphenyl)-propyl chloride. B.p. 102° C./3 mm Hg.

At 0° C. a solution of 10 g AlCl₃ in 10 g nitromethane is added to 8 g of this chloride and 8 g trimethyl ethene in 75 ml cyclohexane in the course of which the temperature raises to approximately 20° C.

When the temperature has dropped to 0° C. 12 g acetyl chloride is added followed by a solution of 20 g AlCl₃ in 100 g nitromethane. After that the reaction mixture is stirred at room temperature during one hour, poured out into ice and extracted three times with ether. The solution in ether is washed neutral, dried on MgSO₄ and evaporated. The residue is distilled under diminished pressure, yielding 9.2 g 6-acetyl-1-isopropyl-5-ethyl-2,3,3-trimethyl indan. B.p. 150° C./1 mm Hg.

EXAMPLE VI

Preparation of 6-acetyl-1-isopropyl-2,2,3,3,5-pentamethyl indan according the reaction schemes of FIG. 1 and FIG. 8

At 0°–10° C. a solution of 8 g AlCl₃ in 30 ml nitromethane is dropped to 7.5 g 2-methyl-1-(p-tolyl)-propyl chloride (obtained as intermediate in Example I) and 4 g tetramethyl ethene.

The reaction mixture is then stirred during 30 min., after which 4 g acetyl chloride is dropwise added at 0°–10° C. Then the reaction mixture is stirred during one hour, poured out into ice and extracted with ether. The solution in ether is washed neutral, dried and evaporated. The residue is distilled under diminished pressure yielding 8.5 g 6-acetyl-1-isopropyl-2,2,3,3,5-pentamethyl indan. B.p. 148°–150° C./1 mm Hg.

EXAMPLE VII

Preparation of 6-acetyl-1-isopropyl-5-ethyl-2,2,3,3-tetramethyl indan according to the reaction schemes of FIG. 1 and FIG. 8

A solution of 8 g AlCl₃ in 30 ml nitromethane is added to 8 g 2-methyl-1-(p-ethylphenyl)-propyl chloride (obtained as intermediate in Example V) and 4 g tetramethyl ethene. Further the reaction mixture is treated with acetyl chloride and worked up as in Example VI. Yield: 8.3 g 6-acetyl-1-isopropyl-5-ethyl-2,2,3,3-tetramethyl indan. B.p. 149°–150° C./1 mm Hg.

EXAMPLE VIII

Preparation of 2,3,3,5-tetramethyl-1-indanone according to the reaction scheme of FIG. 3

100 g Tin (IV) chloride is added at 10° C. to a solution of 79 g p-methyl benzoyl chloride and 40 g trimethyl ethene in 100 ml cyclohexane. The reaction mixture is then stirred at 10° C. during 30 min., subsequently poured out into ice and extracted with ether. The solution in ether is washed neutral, dried and evaporated. The residue is added to a solution of 72 g AlCl₃ in 200 ml nitropropane, in the course of which the temperature is kept at 25°–30° C. Then the reaction mixture is stirred during five hours at 20° C. After that it is poured out into ice and extracted with ether. The solution in ether is washed neutral, dried and evaporated. The residue is distilled under diminished pressure yielding 45.4 g of the desire indanone. B.p. 95° C./1 mm Hg.

EXAMPLE IX

Preparation of 6-acetyl-1-isopropyl-2,3,3,5-tetramethyl indan according to the reaction scheme of FIG. 4

To a solution of 30 g isopropyl magnesium bromide in 300 ml ether is added 20 g indanone (obtained according to Example VIII). Then the reaction mixture is stirred during one hour and poured out into a mixture of ice and NH₄Cl. The layers are separated and the aqueous layer is extracted with ether. The solution in ether is dried and then during one hour gaseous HCl is introduced. The solution is dried once again and evaporated.

The residue is distilled under diminished pressure yielding 3.4 g of the desired chloride. B.p. 70°–80° C./1 mm Hg. This is dissolved in 25 ml methanol, 5 ml triethyl amine is added and the reaction mixture is hydrogenated at 50° C. in the presence of 100 mg 5% Pd on carbon as a catalyst. Evaporating the reaction mixture yields 1-isopropyl-2,3,3,5-tetramethyl indan, which is then acetylated as described in Example III to obtain a mixture of 85–90% by weight cis- and 10–50% by weight trans-6-acetyl-1-isopropyl-2,3,3,5-tetramethyl indan. This mixture can be separated by means of gas-liquid-chromatography, column: 2 m, 10% by weight silicon oil type OV17 (Varian); temp. 200° C.

EXAMPLE V

Preparation of
6-acetyl-1-trimethylsilyl-2,3,3,5-tetramethyl indan
according to the reaction scheme of FIG. 5

20 g Indanone (obtained according to Example VIII) is added to a solution of 1.5 molequivalent $NaAlH_2$ $(OC_2H_4OCH_3)_2$ in a mixture of benzene and ether in the course of which the temperature raises to 35° C. Then the reaction mixture is stirred during one hour, poured out into ice and extracted with ether. The solution in ether is washed with NaCl solution, dried and evaporated. The residue is distilled under diminished pressure yielding 15.1 g indanol. B.p. 115° C./1 mm Hg. The indanol is dissolved in 100 ml cyclohexane and during 30 min. gaseous HCl is introduced followed by $N_2$ to remove the excess of HCl. The reaction mixture is evaporated and the residue is distilled under diminished pressure yielding 12.9 g indanyl chloride. B.p. 95° C./1 mm Hg.

A mixture of 12.5 g indanyl chloride and 10 g dibromoethane is added to 7 g magnesium in 150 ml tetrahydrofuran in the course of which the temperature is kept at 50° C. The mixture is subsequently stirred during one hour. Then 15 g trimethylsilyl chloride is added and the reaction mixture is heated to reflux, after that poured out into ice and extracted with ether. The solution in ether is dried and evaporated. The residue is distilled under diminished pressure yielding 3 g 1-trimethylsilyl-2,3,3,5-tetramethyl indan. B.p. 110° C./1 mm Hg. This compound is dissolved in cyclohexane and acetylated with acetyl chloride under the influence of 2 equivalents $AlCl_3$, as is described in Example III. The obtained 6-acetyl-1-trimethylsilyl-2,3,3,5-tetramethyl indan is purified by means of preparative gas-liquid-chromatography with the use of a column of 2 m with 10% by weight silicon oil type OV17 (Varian), temp.: 200° C.

EXAMPLE XI

Preparation of 6-acetyl-1-tert.butyl-2,3,3,5-tetramethyl indan according to the reaction scheme of FIG. 6

85 g p-methyl benzaldehyde is added to a solution of tert.butyl magnesium chloride in ether, prepared from 15 g magnesium and 60 g tert.butyl chloride.

The mixture is stirred during one hour, then poured out into a mixture of ice and diluted hydrochloric acid and extracted three times with ether. The solution in ether is dried and then gaseous HCl is introduced during one hour. The solution in ether is evaporated and the residue is dissolved in cyclohexane. It is cycloalkylated with trimethyl ethene under the influence of $AlCl_3$ and acetylated with acetyl chloride, also under the influence of $AlCl_3$, as is described in Example V. To isolate 6-acetyl-1-tert.butyl-2,3,3,5-tetramethyl indan the raw reaction product is separated by means of preparative gas-liquid-chromatography, as is described in Example X.

EXAMPLE XII

Preparation of 6-formyl-1-isopropyl-2,3,3,5-tetramethyl indan according to the reaction scheme of FIG. 7

40 ml Bromine is added at 10° C. to a solution of 100 g 1-isopropyl-2,3,3,5-tetramethyl indan (obtained according to Example I or II) and 1 ml pyridine in 50 ml carbon tetrachloride. Then the reaction mixture is stirred during one hour and poured out into an aqueous solution of approximately 25 g sodium thiosulphate. The organic layer is separated, washed with 25% sodium hydroxide and evaporated. The residue is distilled under diminished pressure yielding 105 g 6-bromo-1-isopropyl-2,3,3,5-tetramethyl indan. B.p. 145°–150° C./1 mm Hg. 25 g Dimethyl formamide is added to a solution of 1-isopropyl-2,3,3,5-tetramethyl-6-indanyl magnesium bromide, prepared from 9 g magnesium and 100 g of the 6-bromo indan obtained above. The reaction mixture is then heated to reflux during 30 min., poured out into a mixture of ice and diluted sulphuric acid and extracted with ether. The solution in ether is washed neutral, dried and evaporated. The residue is distilled under diminished pressure yielding 30 g 6-formyl-1-isopropyl-2,3,3,5-tetramethyl indan. B.p. 135° C./1 mm Hg.

EXAMPLE XIII

A perfume composition of the Muguet-type to be used in detergents was prepared according to the following recipe:

| | |
|---|---|
| 10 parts by weight | tetrahydrolinalool |
| 5 parts by weight | isocyclocitral |
| 80 parts by weight | linalool |
| 40 parts by weight | citronellol |
| 10 parts by weight | geraniol |
| 15 parts by weight | aubepin |
| 30 parts by weight | phenyl propanol |
| 20 parts by weight | tridecenyl acetate |
| 10 parts by weight | heliotropin |
| 170 parts by weight | hexyl saolicylate |
| 180 parts by weight | α-hexyl cinnamic aldehyde |
| 120 parts by weight | terpineol |
| 20 parts by weight | 2-methyl-3-(p-tert.butylphenyl)-propanol |
| 60 parts by weight | 4-tert.butyl-cyclohexyl acetate |
| 30 parts by weight | methylionone |
| 200 parts by weight | 6-acetyl-1-isopropyl-2,3,3,5-tetramethyl indan |
| 1000 parts by weight | |

EXAMPLE XIV

A perfume composition of the Muguet-type to be used in detergents was prepared according to the following recipe:

| | |
|---|---|
| 20 parts by weight | musk ketone |
| 20 parts by weight | 2-phenyl ethyl pyridine |
| 30 parts by weight | 2-phenyl ethanol |
| 30 parts by weight | allyl-3-methyl butoxy acetate |
| 50 parts by weight | allyl-heptanoate |
| 250 parts by weight | tridecanol |
| 300 parts by weight | terpineol |
| 50 parts by weight | 4-tert.butyl-cyclohexyl acetate |
| 50 parts by weight | benzyl salicylate |
| 50 parts by weight | hexyl salicylate |
| 150 parts by weight | 6-acetyl-1-isopropyl-2,3,3,5- |

| | |
|---|---|
| | tetramethyl indan |
| 1000 parts by weight | |

Instead of 6-acetyl-1-isopropyl-2,3,3,5-tetramethyl indan, 6-acetyl-1-isopropyl-2,2,3,3,5-pentamethyl indan, 6-acetyl-1-isopropyl-5-ethyl-2,2,3,3-tetramethyl indan or 6-acetyl-1-isopropyl-5-ethyl-2,3,3-trimethyl indan could be used with success in this composition.

EXAMPLE XV

The odour strength of the compound of the formula 5a according to the invention and that of the compounds of the formulae 3 and 4 of the formula sheet were compared mutually. For that purpose two solutions of a different concentration of each of the three fragrances in diethyl phthalate were compared by 20 human subjects with a standard series of four solutions of different strength of n-butanol in diethyl phthalate. The olfactory values awarded by these persons were statistically processed. From that it appears that the compound according to the invention was judged somewhat stronger than the compound of the formula 4 and considerably stronger than the compound of the formula 3.

The experiment was repeated with solutions in water. Again the compound according to the invention showed to be stronger than the compound of the formula 4 and considerably stronger than the compound of the formula 3.

EXAMPLE XVI

A perfume composition of the Lavendel-Fougère-type to be used in toilet soap was prepared according to the following recipe:

| | |
|---|---|
| 230 parts by weight | lavender oil |
| 150 parts by weight | bergamot oil |
| 150 parts by weight | 2-n-butyl-4,4,6-trimethyl-1,3-dioxan |
| 80 parts by weight | petit grain oil |
| 50 parts by weight | hexyl benzoate |
| 50 parts by weight | benzyl salicylate |
| 50 parts by weight | rosmary oil Spanish |
| 50 parts by weight | geranium oil |
| 50 parts by weight | vetiveryl acetate |
| 40 parts by weight | patchuli oil |
| 20 parts by weight | mousse de chêne absolue |
| 15 parts by weight | coumarin |
| 15 parts by weight | lavandin concrète |
| 10 parts by weight | tetrahydrolinalool |
| 5 parts by weight | eugenol |
| 5 parts by weight | labdanum absolue Spanish |
| 5 parts by weight | galbanum resinoid |
| 25 parts by weight | 6-propionyl-1-isopropyl-2,3,3,5-tetramethyl indan |
| 1000 parts by weight | |

Instead of 6-propionyl-1-isopropyl-2,3,3,5-tetramethyl indan, 6-acetyl-1-trimethylsilyl-2,3,3,5-tetramethyl indan or 6-formyl-1-isopropyl-2,3,3,5-tetramethyl indan could be used with success in this composition.

We claim:

1. A perfume composition comprising 6-acetyl-1-isopropyl-2,3,3,5-tetramethyl indan as a fragrance component in combination with at least one auxiliary substance selected from the group consisting of conventional perfume fragrances, mixtures thereof and perfume solvents.

2. The compound 6-acetyl-1-isopropyl-2,3,3,5-tetramethyl indan.

* * * * *